(12) United States Patent  (10) Patent No.: US 8,668,925 B2
Langguth et al.  (45) Date of Patent: Mar. 11, 2014

(54) TRANSDERMAL DELIVERY OF HORMONES WITHOUT THE NEED OF PENETRATION ENHANCERS

(75) Inventors: Thomas Langguth, Jena (DE); Stefan Bracht, Jena (DE); Michael Dittgen, Apolda (DE); Petra Huber, Munich (DE); Dirk Schenk, Dietramszell (DE)

(73) Assignee: Bayer Intellectual Property GmbH, Monheim (DE)

( * ) Notice: Subject to any disclaimer, the term of this patent is extended or adjusted under 35 U.S.C. 154(b) by 1573 days.

(21) Appl. No.: 11/008,642

(22) Filed: Dec. 10, 2004

(65) Prior Publication Data

US 2005/0142175 A1  Jun. 30, 2005

Related U.S. Application Data

(60) Provisional application No. 60/528,718, filed on Dec. 12, 2003.

(51) Int. Cl.
*A61F 13/00* (2006.01)
*A61K 9/70* (2006.01)
*A61F 13/02* (2006.01)
*A61L 15/16* (2006.01)

(52) U.S. Cl.
USPC .......................... 424/449; 424/448; 424/443

(58) Field of Classification Search
None
See application file for complete search history.

(56) References Cited

U.S. PATENT DOCUMENTS

| 5,023,084 A | 6/1991 | Chien et al. |
| 5,106,891 A | 4/1992 | Valet et al. |
| 5,128,124 A | 7/1992 | Fankhauser et al. |
| 5,128,284 A | 7/1992 | Olson et al. |
| 5,352,457 A | 10/1994 | Jenkins |
| 5,376,377 A | 12/1994 | Gale et al. |
| 5,512,292 A | 4/1996 | Gale et al. |
| 5,538,736 A | 7/1996 | Hoffmann et al. |
| 5,560,922 A | 10/1996 | Chien et al. |
| 5,788,984 A | 8/1998 | Guenther et al. |

(Continued)

FOREIGN PATENT DOCUMENTS

| CA | 2 372 710 | 8/2000 |
| CA | 2 366 859 | 9/2001 |

(Continued)

OTHER PUBLICATIONS

"Low doses of estradiol in combination with gestodene to prevent postmenopausal bone loss", American Journal of obstetrics and gynaecology, vol. 183, issue 3, Sep. 2000, pp. 550-560, Bjarnason et al.*

(Continued)

*Primary Examiner* — Isis Ghali
(74) *Attorney, Agent, or Firm* — Millen, White, Zelano & Branigan, P.C.

(57) ABSTRACT

The present invention relates to a patch comprising a drug-containing layer with low content of hormones, such as gestodene, and optionally an estrogen (e.g. ethinyl estradiol). Upon administering the patch to a woman, plasma levels of at least 1.0 ng/ml of Gestodene is achieved at steady state conditions without the need of incorporating penetration enhancers or permeation enhancers in the drug-containing layer. Satisfactorily plasma levels of the hormones is also achieved throughout a period of at least 1 week, making the patch applicable for being used in female contraception with the concept of administering the patch ones weekly.

22 Claims, 1 Drawing Sheet

(56) References Cited

U.S. PATENT DOCUMENTS

| | | | |
|---|---|---|---|
| 5,858,394 A | 1/1999 | Lipp et al. | |
| 5,866,157 A | 2/1999 | Higo et al. | |
| 5,876,746 A * | 3/1999 | Jona et al. | 424/449 |
| 5,904,931 A | 5/1999 | Lipp et al. | |
| 5,906,830 A | 5/1999 | Farinas et al. | |
| 5,948,433 A | 9/1999 | Burton et al. | |
| 6,071,531 A | 6/2000 | Jona et al. | |
| 6,143,319 A * | 11/2000 | Meconi et al. | 424/448 |
| 6,238,284 B1 | 5/2001 | Dittgen et al. | |
| 6,521,250 B2 | 2/2003 | Meconi et al. | |
| 6,902,741 B1 | 6/2005 | Grawe et al. | |
| 6,924,410 B2 | 8/2005 | Tsuruda et al. | |
| 7,470,452 B1 | 12/2008 | Flosbach et al. | |
| 7,687,554 B2 | 3/2010 | Schellenberg et al. | |
| 8,173,592 B1 | 5/2012 | Engel et al. | |
| 2002/0004065 A1 | 1/2002 | Kanios | |
| 2003/0149385 A1 | 8/2003 | Tsuruda et al. | |
| 2003/0152616 A1 | 8/2003 | Hartwig | |
| 2004/0022836 A1 | 2/2004 | Degen et al. | |
| 2005/0055975 A1 | 3/2005 | Tackett et al. | |
| 2005/0142175 A1 | 6/2005 | Langguth et al. | |
| 2005/0175678 A1 | 8/2005 | Breitenbach et al. | |
| 2006/0246122 A1 | 11/2006 | Langguth et al. | |
| 2006/0251707 A1 | 11/2006 | Schumacher et al. | |
| 2006/0287416 A1 | 12/2006 | Schellenberg et al. | |

FOREIGN PATENT DOCUMENTS

| | | |
|---|---|---|
| CA | 2 605 112 | 11/2006 |
| DE | 43 36 299 | 5/1995 |
| DE | 44 03 487 | 8/1995 |
| DE | 199 06 152 | 8/2000 |
| DE | 199 12 623 | 9/2000 |
| DE | 100 53 375 | 1/2002 |
| EP | 285 563 | 10/1988 |
| EP | 0 483 370 | 3/1995 |
| EP | 0 787 488 | 8/1997 |
| EP | 0 976 405 | 2/2000 |
| EP | 1 121 941 | 8/2001 |
| EP | 1 197 212 | 4/2002 |
| EP | 1 269 999 | 1/2003 |
| EP | 1 452 173 | 9/2004 |
| EP | 1 541 137 | 6/2005 |
| JP | 59 039827 | 3/1984 |
| JP | 60 069014 | 4/1985 |
| JP | 60 1966611 | 8/1985 |
| JP | 1026537 | 1/1989 |
| JP | 6 93217 | 4/1994 |
| JP | 09 315957 | 12/1997 |
| JP | 10-265371 | 10/1998 |
| JP | 2002 541122 | 12/2002 |
| JP | 5 30118 | 3/2004 |
| JP | 4 504109 | 7/2010 |
| WO | WO 90/04397 | 5/1990 |
| WO | WO-90 06736 | 6/1990 |
| WO | WO 92/07590 | 5/1992 |
| WO | WO-96 40355 | 12/1996 |
| WO | WO-97 38354 | 10/1997 |
| WO | WO 97/39743 | 10/1997 |
| WO | WO-99 66908 | 12/1999 |
| WO | WO 00/45797 | 8/2000 |
| WO | WO-00/56289 | 9/2000 |
| WO | WO-00 59542 | 10/2000 |
| WO | WO 01/37770 | 5/2001 |
| WO | WO-01/68061 | 9/2001 |
| WO | WO 02 34200 | 5/2002 |
| WO | WO 02 45701 | 6/2002 |
| WO | WO-03 077925 | 9/2003 |
| WO | WO-2004 058247 | 7/2004 |
| WO | WO-2004 073696 | 9/2004 |
| WO | WO-2005 023878 | 3/2005 |
| WO | WO-2005 058207 | 6/2005 |
| WO | WO-2006 117139 | 11/2006 |
| WO | WO-2010 042152 | 4/2010 |

OTHER PUBLICATIONS

Partial European Search Report dated Sep. 27, 2005.
European Search Report dated May 12, 2004.
R. Sitruk-Ware, "Transdermal Application of Steroid Hormones for Contraception", J. Steroid Biochem. Molec. Biol. vol. 53, No. 1-6, pp. 247-251, 1995.
Brisaert, M. et al., "Investigation on the photostability of a tretinoin lotion and stabilization with additives," Proc. $2^{nd}$ World Meeting on Pharmaceutical Technology, APGI/APV, Paris, 25/28, May 1998, pp. 1231-1232.
Chatelain, Eric et al., "Photostabilization of Butyl Methozydibenzoylmethane . . . " Photochemistry and Photobiology, 2001, vol. 74, No. 3, pp. 401-406 (English).
Ciba Specialty Chemicals Tinosorb S brochure (2002).
Sekisui Chem Co Ltd., "Transcutaneous Absorption Plaster," Patent Abstracts of Japan, Publication Date: Jun. 10, 1998; English Abstract of JP-10-265371.
Thomson Innovation, English Translation of Claims and Description, Retrieved from Thomson Innovation Record View on Jun. 14, 2010; English Abstract of DE4336299.
Thomson Innovation, English Translation of Claims and Description, Retrieved from Thomson Innovation Record View on Jun. 14, 2010; English Abstract of DE4403487.
Thomson Innovation, English Translation of Claims and Description, Retrieved from Thomson Innovation Record View on Jun. 14, 2010; English Abstract of DE19912623.
Thomson Innovation, English Translation of Claims and Description, Retrieved from Thomson Innovation Record View on Jun. 14, 2010; English Abstract of WO2000056289.
Thomson Innovation, English Translation of Claims and Description, Retrieved from Thomson Innovation Record View on Jun. 14, 2010; English Abstract of EP1452173.
Hisamitsu Pharmaceut Co Inc., "Device for Percutaneous Therapy," Patent Abstracts of Japan, Publication Date: Dec. 9, 1997; English Abstract for JP-09 315957.
Sekisui Chem Co Ltd., "Transcutaneous Absorption Plaster," Patent Abstracts of Japan, Publication Date: Oct. 6, 1998; Full English Translation of1 of JP-10-265371.
Sanken Kako KK, "Production of dibenxyls," Patent Abstracts of Japan, Publication Date: Jan. 27, 1989, English Abstract of JP-10-26537.
Thomas Innovation, English Abstract of WO-1990 004397, Publication Date: May 3, 1990.
Translation of Abstract of JP-530118, Publication Date: Mar. 10, 2004.
Translation of Abstract of JP-59039827, Publication Date: Apr. 19, 1985.
Translation of Abstract of JP-60166611, Publication Date: Aug. 29, 1985.
Shinyosha KK, "Image display apparatus and pixel constituent," Patent Abstracts of Japan, Publication Date: Jan. 5, 2006; English Abstract of JP-4 504109.

* cited by examiner

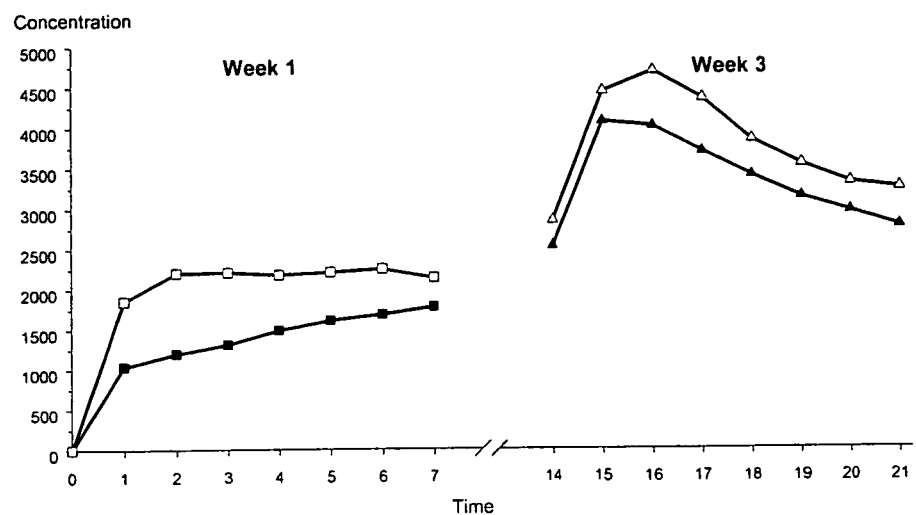

TRANSDERMAL DELIVERY OF HORMONES WITHOUT THE NEED OF PENETRATION ENHANCERS

This application claims the benefit of the filing date of U.S. Provisional Application Ser. No. 60/528,718 filed Dec. 12, 2003, which is incorporated by reference herein.

FIELD OF INVENTION

The present invention relates to the field of pharmaceutical formulation techniques. The invention provides a low dosage pharmaceutical composition for transdermal delivery of at least one hormone, preferably a progestin, such as a gestodene, and optionally an estrogen, so as to achieve plasma concentration profiles effective in inhibiting ovulation in a woman.

BACKGROUND

Transdermal delivery of estrogens and progestins for providing contraception is a known concept (Sitruk-Ware, Transdermal application of steroid hormones for contraception, 3 Steroid Biochem Molecul Biol, Volume 53, p 247-251). However, estrogens and progestins do generally poorly penetrate the skin, for which reason it is common, in transdermal systems, to incorporate agents with skin penetrating enhancing effect.

The following documents describe a number of transdermal systems with a progestin and an estrogen present in the adhesive layer and wherein the need of penetration enhancers is emphasised:

WO 92/07590 describes compositions with penetration enhancers for the transdermal delivery of Gestodene and an estrogen so as to achieve maximal plasma levels of Gestodene of about 0.9 ng/ml.

WO 97/397443 relates to a transdermal system containing between 30 to 60% of penetration enhancers so as to deliver a contraceptively effective amount of an estrogen and a progestin.

WO 01/37770 relates to transdermal systems containing between 10 to 60% of penetration enhancers for delivery of Ethinylestradiol and Levonorgestrel in contraceptively effective amounts.

U.S. Pat. No. 5,512,292 is directed to compositions comprising a contraceptively effective amount of Gestodene and an estrogen, such as Ethinylestradiol, together with a suitable permeation enhancer. The amount of the estrogen co-delivered is kept at a constant and contraceptive effective rate while the amount of Gestogen co-delivered varies depending on the phase of the menstrual cycle.

In U.S. Pat. No. 5,376,377 comparable studies between transdermal systems with and without penetration enhancers are shown. The studies include an adhesive layer made of ethylene vinyl acrylate and as the active ingredient, Gestodene and an estrogen (ethinylestradiol). The study results indicate the need of incorporation penetration enhancers in the adhesive layer so as to achieve contraceptive effective amounts. Maximal plasma levels of about 0.8 ng/ml were achieved.

Finally, WO 90/04397 also discloses examples of compositions for transdermal delivery of gestodene, optionally in combination with an estrogen, such as Ethinylestradiol, wherein the composition further may comprise a penetration enhancer, such as 1,2-propandiol or isopropylmyristat. As adhesive layer is mentioned a number of various polymers. Examples on polar polymers (polyacrylates and silicones) in combination with a penetration enhancer are specifically disclosed. The resulting plasma levels of Gestodene at steady state conditions were approx. 250 to 337 pg/ml.

In addition to penetration enhancers, it is also suggested to add solubilising agents or the like to the drug-containing layer in order to increase the amount of dissolved drug or to add agents inhibiting the crystallisation of the drug in the layer.

For example, in U.S. Pat. No. 6,521,250 is disclosed an adhesive layer that comprises a mixture of styrene-isoprene block copolymer and a hydrogenated resin acid or its derivatives, the amount of the resin being of 55-92%. Such an adhesive layer seems suitable for the transdermal delivery of estradiol in combination with a progestin in that such systems have a proper adhesive contact with the skin for long-term application and prevent crystallisation of the hormones.

U.S. Pat. No. 5,904,931 relates to TTS systems containing in the drug-containing layer a steroid (such as Gestodene) and dimethyl isosorbide. The latter enhances the solubility of the steroid in the drug-containing layer. The concentration of the Gestodene in the drug-containing layer may vary from 1-40% by weight of the layer and the drug-containing layer may consist of adhesives such as polyacrylates, silicones, styrene-butadiene co-polymers and polyisobutylenes. Especially, polar polymers, such as polyacrylates, are suitable.

DE 199 06 152 relates to a transdermal drug delivery system in which Gestodene is embedded in a polar polymer, such as polyvinylpyrrolidone, methylcellulose, ethylcellulose, and hydroxypropylcellulose, previous to being added to an adhesive polymer, such as polyisobutylene. Thus, this transdermal drug delivery system is a twophase system and the drug-containing layer is not transparent because of the content of the polar polymers, which upon exposure to water will result in the presence of milky-white spots. The amount of Gestodene in the drug-containing layer is 5.1% by weight of the drug-containing layer.

In WO 02/45701 it is emphasised that the addition of a rosin ester in an amount up to 25% by weight to an adhesive layer may sufficiently suppress crystal formation of active agents such as for example hormones. The adhesive layer may include all non-toxic natural and synthetic polymers known and which are suitable for use in transdermal systems, for example polyacrylates, polysiloxanes, polyisobutylenes, styrene block copolymers and the like. Particularly, polyacrylates are emphasised. The TTS system is suitable for steroids (Gestodene), which may be incorporated in the adhesive layer in an amount substantially at or near or even above the saturation with respect to their concentration in the carrier composition rather than substantially at subsaturation. Preferably, the amount of the steroid is from about 0.1% to about 6% by weight, based on the dry weight of the total carrier composition.

Unfortunately, penetration enhancers may adversely affect the skin such as irritating the skin, which to some extend renders transdermal systems unacceptable for the user. Additionally, it is generally known that penetration enhancers may negatively affect the stability of active substances rendering long-term storage problematic. Furthermore, it is also recognised that the viscosity is reduced by incorporation of penetration enhancers resulting in the risk of formation of dark rings along the edges of the patch.

Therefore, there is a need for transdermal systems without the above-mentioned. drawbacks, such as transdermal systems that do not require penetration enhancers for achieving therapeutically effective amounts of a steroidal hormone, such as Gestodene.

Gestodene is a known orally active synthetic progestin with a progesterone-like profile of activity (see, U.S. Pat. No. 4,081,537). It is used as an oral contraceptive in combination with certain estrogens.

SUMMARY OF THE INVENTION

This invention relates to compositions suitably formulated for transdermal delivery of hormones, so that contraceptively effective levels are achieved without the need of incorporating penetration enhancers in the hormone-containing adhesive layer. The actual hormones are preferably steroidal hormones, such as progestins, such as a Gestodene, which optionally may be used in combination with an estrogen. Unlike the general knowledge in the art, the present inventors have provided transdermal systems comprising a limited number of ingredients. For example penetration enhancers and or permeation enhancers are not required in order to achieve high release rate and therapeutically effective plasma levels.

The present inventors have found that the selection of a drug-containing layer that has a solubility for the steroidal hormone (e.g. Gestodene) is critical for the successful achievement of therapeutically effective levels of a hormone in the blood. Example 2 herein shows the comparison of two Gestodene-containing layers with respect to their release rate of Gestodene. It is clearly demonstrated that a drug-containing layer of a polar polymer (polyacrylate) requires a concentration of Gestodene of 3.9% by weight of this layer to achieve the desired high release rate. Surprisingly, and in contradiction to what has previously been known, the same high release rate can be achieved with a concentration of 1.9% by weight of Gestodene in a drug-containing layer comprising a less polar polymer, such as polyisobutylene, even without the use of a penetration enhancer. Also in-vivo studies have revealed that drug-containing layers containing the more non-polar type of polymer such as the polyisobutylene in preference to the polyacrylates are better in terms of achieving high plasma AUC (Example 4)

Thus, the present inventors have found, unlike what could be expected, that the use of drug-containing layers preferably containing a apolar polymer, such as polyisobutylenes, and characterised by having a limited solubility with respect to Gestodene of no more than 3% by weight have a high release rate of Gestodene despite the actual load of Gestodene in the drug-containing layer is low. This is clearly an advantage over the previously known TTS systems in terms of decreasing the risk of skin irritation, decreasing the exposure of hormone to the user and to the environment.

A further advantage is that the drug-containing layer is a monophasic system and contains the drug evenly distributed throughout the layer. That is to say that the drug-containing layer is homogenous. In absence of polar polymers or other polar additives with tendency to absorb water or to retain water, the drug-containing layer is transparent. Thus, a transparent composition, wherein the skin can be visually inspected through the drug delivery system, has been provided by the present invention. Transparency of a transdermal drug delivery system is a clear advantage for the user because non-transparent systems are visible and thus indicate sickness, which is not the intention with a contraceptive patch.

Accordingly, a first aspect of the invention relates to compositions for transdermal delivery of a steroidal hormone, preferably a progestin, such as Gestodene or a derivative thereof (ester thereof), and optionally an estrogen. The composition comprises a drug-containing layer comprising said hormone and one or more pharmaceutically acceptable excipients or carriers, and the drug-containing layer having a solubility for said hormones (such as Gestodene) of no more than 3% by weight of the drug-containing layer.

In a particular aspect thereof, the invention relates to a composition comprising a progestin, such as Gestodene or a derivative thereof, and a polymer in an amount of from about 15 to 99% by weight of the drug-containing layer, the polymer being selected from the group consisting of hydrocarbon polymers, polysiloxanes, poly-acrylates and mixtures thereof that form a drug-containing layer having a solubility for Gestodene of no more than 3% by weight of the drug-containing layer.

In another particular aspect thereof, the invention relates to compositions comprising a drug-containing layer consisting essentially of a progestin such as Gestodene or a derivative thereof, a polymer in an amount of from about 15 to 99% by weight of the drug-containing layer, a tackifier, such as a rosin ester in an amount of up to 85% by weight, such as in an amount in the range of 1-85% of the drug-containing layer, and optionally an estrogen.

In a still particular aspect, the invention relates to a composition for transdermal delivery comprising a drug-containing layer that comprises:
i) a progestin, preferably a Gestodene or derivative thereof, such as an ester thereof; and
ii) a polymer selected from the group consisting of polyisobutylenes, polybutenes, polyisoprenes, polystyrenes, styrene isoprene styrene block polymers, styrene butadiene styrene block polymers and mixtures thereof.

A still particular aspect of the invention relates to a transparent composition for transdermal delivery, the composition comprises a drug-containing layer that comprises a progestin, preferably a Gestodene or derivative thereof (such as an ester thereof) and the drug-containing has a solubility for Gestodene of no more than 3% by weight of the drug-containing layer.

It has surprisingly been found that relatively high plasma levels of Gestodene can be maintained for a prolonged period of time by administering a Gestodene formulated in a composition of the invention. The plasma profile and plasma levels of Gestodene, as resulting from the administration of a Gestodene and optionally an estrogen, are effective in inhibiting the ovulation in a woman.

Therefore compositions of the invention may be used for inhibiting ovulation or alternatively for the treatment of endometriosis, pre-menstrual syndrome, climacteric disorders, prevention of osteoporosis, regulating the menstrual cycle or stabilising the menstrual cycle.

Thus, in still further aspects, the invention relates to the use of a composition as described herein optionally in combination with an estrogen, for inhibition of ovulation in a female. When the composition is singly administered, then a plasma concentration-time curve of Gestodene is achieved characterised by having plasma levels of Gestodene in a concentration of at least 1.0 ng/ml, as determined at steady state conditions. In association herewith, the invention relates to a method for inhibiting ovulation in a female, such as a woman. The method comprises administering topically to the skin or mucosa an effective amount of Gestodene or a derivative thereof, optionally in combination with an estrogen, so as upon singly administering said Gestodene, then a plasma concentration-time curve of Gestodene is achieved characterised by having plasma levels of Gestodene in a concentration of at least 1.0 ng/ml, as determined at steady state conditions.

Finally, the invention relates to a kit comprising 1 to 11 dosage units, such as 9 or 3 dosage units, dependent on the length of the treatment period, formulated in a form for transdermal delivery of Gestodene or a derivative thereof, such in a form of a composition as described herein. The dosage form comprising a drug-containing layer comprising Gestodene and one or more pharmaceutically acceptable excipients or carriers, wherein the drug-containing layer has a solubility with respect to Gestodene of no more than 3% by weight of the drug-containing layer.

DETAILED DESCRIPTION

The invention provides compositions for transdermal delivery of hormones (transdermal therapeutic system) that upon topical application to the skin or a to a mucosa results in therapeutically effective amounts, such as contraceptively effective amounts of the hormones, although skin penetration enhancers are not necessarily incorporated in the drug-containing layer.

As used herein, the term "topical" or "topically" denotes the direct contact of the composition with a surface area of a mammal including skin and mucosa.

The term "mucosa" means any surface membrane on a mammal, which is not skin, such as a surface present in the buccal cavity, vagina, rectum, nose or eye. Thus, the mucosa may be buccal, vaginal, rectal, nasal or ophthalmic mucosa.

The compositions of the invention may be designed in several various application forms provided that the composition comprises a drug-containing layer, which is adapted to be placed near to or in direct contact with skin or mucosa upon topically administering the composition.

Therefore, in a preferred application form, the composition, e.g. the transdermal therapeutic system, consists essentially of
 a) a backing layer;
 b) at least one drug-containing layer comprising said hormone or a mixture of said hormones and one or more pharmaceutically acceptable ingredients; and
 c) optionally a removable release liner or protective layer Preferably, the backing layer, the drug-containing layer and the removable release liner (or protective layer) are transparent, which means that the skin is visible.

In case the drug-containing layer fails to exhibit sufficient self-tackiness to the skin or mucosa, it may be provided with an additional layer of a pressure-sensitive adhesive layer or with a pressure-sensitive adhesive edge or ring so as to ensure adherence of the composition to the skin over the whole application period. The pressure-sensitive adhesive layer may be located between the drug-containing layer and the skin and the adhesive ring may be located around or at the edge of the drug-containing layer. Optionally, the composition may also additionally comprise one or more membranes or adhesive layers. For example, a membrane for controlling the release of the hormones can be located between the drug-containing layer and the pressure sensitive layer or between the drug-containing layer and the skin.

The size of the drug-containing layer is selected from a variety of reasonable sizes. As used herein, a reasonable size is meant to be a surface area of from about 5 to 20 $cm^2$, preferably of from about 7 to 15 $cm^2$, most preferably of from about 8 to 12 $cm^2$, such as 10 $cm^2$. Notably, the surface area is the area that is in contact with or in close proximity to the skin or mucosa.

According to the invention it is found that a drug-containing layer with minimised solubility for the hormone provides sufficient skin penetration of a steroidal hormone. In the present invention, the drug-containing layer is characterised by defining its solubility for Gestodene. Notably, the skin penetration rate suffices without the need of incorporation of a skin penetration enhancer. For example, it is surprisingly found that the skin penetration of a steroidal hormone of the invention results in therapeutically effective amounts of the steroidal hormone in the circulating blood, such as contraceptively effective amounts of the hormone.

Accordingly, the invention relates in a first aspect to a composition for transdermal delivery of a steroidal hormone, such as a progestin, e.g. Gestodene or a derivative thereof. The composition comprises a drug-containing layer and one or more pharmaceutically acceptable excipients or carriers and the drug-containing layer has a solubility for Gestodene of no more than 3% by weight of the drug-containing layer. The composition may optionally comprise an estrogen.

In some embodiments thereof, the solubility of the drug-containing layer for Gestodene is no more than 2.5% by weight of the drug-containing layer, preferably no more than 2.0%, such as no more than 1.8%. In principle, the solubility could be very low, but it is considered that the critical level with respect to the lowest level of said solubility is about 0.1%, such as about 0.2%, 0.3%, 0.5%, 0.7%, 0.8%, 0.9% or 1% by weight of Gestodene in the drug-containing layer. It is generally considered that the solubility of the drug-containing layer for Gestodene is in the range between about 0.1% and 3%, such as about 0.2% and 3%, 0.4% and3%, 0.5% and 0.3%, 0.8% and 3% or 1% and 3%. In further embodiments thereof, the upper limit in the range is not 3% by weight but lower, such as 2.5% 2.2% or 2.0%.

As used herein, the term "a gestodene" is denoted to mean Gestodene (13β-Ethyl-17α-ethynyl-17β-hydroxy-4,15-gonadien-3-one), a derivative thereof or a mixture thereof, such as mixtures of the derivatives or a mixture of Gestodene and a derivative. The derivative may be a derivative of the 17β-hydroxy group, such as ether, ester, acetal or a pharmaceutically acceptable salt thereof. For example an ester with 2 to 12 carbon atoms in the acyl radical, including alkanoates with 2 to 8 carbon atoms in the alkanoyl radical.

In preferably embodiments of the invention, an ester of Gestodene is Gestodene propionate, Gestodene valerate, and/or Gestodene capronate, which aredescribed in U.S. Pat. No. 5,858,394.

As mentioned, the inventors have found that a suitable drug-containing layer of the invention is one that has solubility for the steroidal hormone (e.g. Gestodene) of no more than 3% by weight of the drug-containing layer.

The phrase "a solubility for a steroidal hormone, such as "a solubility for Gestodene, of no more than 3% by weight of the drug-containing layer" is meant to characterise the quantity of the steroidal hormone, such as Gestodene that can dissolve in a particular drug-containing layer yielding a visually clear solution. The term (a solubility for) should not be understood as meaning the actual concentration of hormone, such as Gestodene, in the drug-containing layer. As described below, the total concentration of hormone in the drug-containing layer may be above or below 3% by weight of the drug-containing layer. Furthermore, the total concentration of hormone in the drug-containing layer may give rise to a drug-containing layer comprising the hormone at saturated or sub-saturated levels.

In order to select drug-containing layers having the specified solubility for a hormone, such as Gestodene, the following test may be carried out in order to determine whether the hormone is completely dissolved and the resulting drug-containing layer is visually clear.

One test method is to determine whether the hormone is completely dissolved in that solid particles cannot be detected visually or by using a microscope having a magnification of 25×.

Another method is to actually determine the the solubility of the drug-containing layer for the hormone by the following method. The method is based on the determination of the release rate constants of the hormone from a drug-containing layer comprising the hormone on completely dissolved form and from a drug-containing layer with the hormone partially dissolved.

The method includes the following steps:

Firstly, identical drug-containing layers, but with various, such as increasing, amounts of the hormone, are to be manufactured. As a rule, at least 3 of the various drug-containing layers should contain the hormone in a form completely dissolved in the drug-containing layer and at least 3 drug-containing layers should contain the hormone as partially dissolved, e.g. with the hormone in the form of solid particles.

As concerning the manufacturing process, the following steps can be followed. Any other method known in the art to manufacture adhesive layers may also be appropriate:

The drug substance is dissolved or suspended in an appropriate solvent.

The polymer, optionally the tackifier and other excipients are dissolved in an appropriate solvent.

The two solutions are combined while stirring, so as to obtain a homogeneous mixture.

The mixture is coated onto a release liner in an appropriate thickness and dried under heat to evaporate the solvents.

The resulting laminate is covered with the backing foil.

Secondly, the release rate of the drug from the drug-containing layer is tested using the equipment and test conditions given in the relevant section of the European Pharmacopoeia (Ph. Eur. 2.9.4. Dissolution test for transdermal patches) or the United States Pharmacopoeia (USP 26, <724> DRUG RELEASE, apparatus 5 (Paddle over Disk).

A sample with a defined area is cut from the drug-containing layer.

After removal of the release liner the sample is placed in a vessel (as described in the Pharmacopoeia mentioned above) which is previously filled with an appropriate dissolution media equilibrated at 32° C.±0.5° C. The drug-containing layer should be in contact with the dissolution media. Samples of the dissolution media are taken at pre-defined time intervals and the amount of hormone dissolved in the dissolution media is measured using HPLC or other appropriate quantification methods. The dissolution media can be selected from those ensuring sink conditions. For example, suitable dissolution media are aqueous solutions containing up to 30% by weight of organic solvents, such as ethanol, isopropanol and dioxane.

Thirdly, the release rate of hormones from the two types of drug-containing layers is determined as follows:

the amount of hormone released per area unit of each of the drug-containing layer is calculated from the dissolution data mentioned above and the specific area of the drug-containing layer.

the release rate constant for each drug-containing layer is determined as the slope obtained by the linear regression analysis of the at last three data points on the amount of hormone per area unit versus the square root of time.

The release-rate constant for each of the drug-containing layers is plotted against the concentration of hormone in the drug-containing layer. Linear regression analysis is then carried out separately for the drug-containing layers with completely dissolved hormone and for drug-containing layers with partially dissolved hormone, i.e. with solid particles of hormone present. The two regression lines will cross each other at a point The concentration of the hormone that can be read at the cross point of the two regression lines denotes the "solubility" of the hormone in the drug-containing layers.

The term "drug-containing layer" is meant to denote that part of the transdermal composition or system wherein the steroidal hormone is present. The drug-containing layer can be in semi-solid or solid form and comprises the hormone formulated directly in the layer. The hormone of the invention may be dispersed, partly dispersed, partly dissolved or fully dissolved in it dependent on the concentration and the physico-chemical properties of the hormone. The drug-containing layer is not meant to be in the form of a gel or a liquid. Intentionally, the drug-containing layer is meant to be in direct contact with the skin or mucosa. However, in some embodiments, there is an additional layer, a so-called no-drug-containing layer, located between the drug-containing layer and the skin or mucosa.

As said, compositions according to the invention do not necessarily comprise a skin penetration enhancer. Thus, in some embodiments of the invention, the drug-containing layer exclude the presence of a skin penetration rate enhancer, which means that the drug-containing layer consists essentially of ingredients not including a skin penetration rate enhancer. This means that for example less than 2%, such as less than 1%, preferably less than 0.50%, such as less than 0.2%, such as less than 0.1% by weight of the drug-containing layer is composed of a skin penetration enhancer.

According to the present invention, the selection of the proper drug-containing layer effects the skin penetration. The proper drug-containing layer is preferably made of a polymer or mixtures of polymers. The polymers may have adhesive properties or may be without noticeable adhesive properties. In some embodiments, the drug-containing layer is a so-called pressure sensitive adhesive layer.

In principle any mixture of polymers resulting in the said solubility for Gestodene may be applied. Thus, in one embodiment of the invention the drug-containing layer comprises at least one polymer that may have adhesive properties or not. Typically, such polymers are biologically acceptable lipophilic polymers of the types of a hydrocarbon polymer, a polysiloxane, a poly-acrylate, or mixtures thereof. Preferably, the polymers may be selected from those hydrocarbon polymers, polysiloxanes and/or poly-acrylates that form a drug-containing layer having a solubility forGestodene, of no more than 3% by weight of the drug-containing layer.

The amount of the polymer is to some extent a critical parameter. The proper amount may depend on the actual type of polymer and the steroidal hormone in use. In general, the amount of the polymer is at least 1% by weight of the drug-containing layer, such as at least 5%, 10%, 15% or 20%. However, preferably, the polymer is present in the drug-containing layer in an amount of at least 25%, 30%, 35%, 40%, 45%, 50%, 55%, 60%, 65%, 70%, 75% or at least 80% by weight of the drug-containing layer. In other words, the polymer can be used in an amount of from about 1 to 99% by weight of the drug-containing layer, such as from about 5 to 99%, 10 to 99%, 15 to 99% or 20 to 99%. Preferably, the polymer is present in the drug-containing layer in an amount ranging from about 15 to 99%, such as from about 15 to 90%, 15 to 85% or 15 to 80%, such as from about 20 to 55%, 20 to 75%, such as from about 25 to 85%, 25 to 75% by weight of the drug-containing layer.

This being said, a particular aspect of the invention is directed to a composition for transdermal delivery of a steroidal hormone, such as a Gestodene or a derivative thereof, and optionally an estrogen, the composition comprising a drug-containing layer that comprises at least one steroidal hormone, such as a Gestodene or a derivative thereof and one or more pharmaceutically acceptable ingredients or carriers;

a polymer or a mixture of polymers, preferably in an amount of from about 15 to 99% by weight of the drug-containing layer, wherein the polymer is being selected from the group consisting of hydrocarbon polymers, polysiloxanes, poly-acrylates and mixtures thereof that form a drug-containing layer having a solubility with respect to said steroidal hormone of no more than 3% by weight of the drug-containing layer.

As mentioned, it has been found that adhesive layers comprising the more non-polar types of polymers, such as the hydrocarbon polymers, have been shown to be superior to the polar type polymers, such as the polyacrylates (Example 2). Therefore in a preferred embodiment of the invention, the drug-containing layer comprises as the polymer a hydrocarbon polymer, which preferably may include polyisobutylenes, polybutenes, polyisoprenes, polystyrenes, styrene isoprene styrene block polymers, styrene butadiene styrene block polymers and/or mixtures thereof.

As mentioned above, in some embodiments of the invention, the drug-containing layer is adhesive. Preferentially, the polymer of the drug-containing layer has suitable adhesive properties so that no further sticky agent, such as a tackifier is required. Whenever it is considered necessary to improve the adhesive strength of the drug-containing layer, the layer further comprises a tackifier.

The term "tackifier" denotes an agent that improves the adhesive strength of the adhesive layer to the skin or mucosa.

Examples of tackifiers are selected from hydrocarbon resins, rosin resins and terpene resins. Examples of hydrocarbon resins are commercially available under the tradename Escorez® from ExxonMobil; Regalite®, Piccotac® and Picco® from Eastman or Indopol® from BP. Examples of rosin esters suitable for transdermal systems according to the present invention include esters of hydrogenated wood rosin e.g. pentaerythritol ester of hydrogenated wood rosin, esters of partially hydrogenated wood rosin e.g. pentaerythritol esters of partially hydrogenated wood rosin, esters of wood rosin, esters of modified wood rosin, esters of partially dimerized rosin, esters of tall oil rosin, esters of dimerized rosin, and similar rosins, and combinations and mixtures thereof. Such rosin esters are commercially available under the tradenames Foral®, Foralyn®, Pentalyn®, Permalyn® and Staybelite®.

In a preferred embodiment of the invention, the drug-containing layer comprises a tackifier in the form of a a rosin ester such as pentaerythritol ester.

It is generally considered that the tackifier can be present in any suitable amount as long as the said critical solubility of the steroidal hormone in the drug-containing layer is not affected noticeable. Thus, a tackifier may be present in the drug-containing layer in an amount of from about 0.1 to 95%, such as 0.5% to 95%, such as 1% to 95% by weight of the drug-containing layer. That is to say that the tackifier can be present in an amount of from about 1% to 85%, 1 to 75%, 1 to 65%, 1 to 55%, 1 to 50%, 1 to 45%, 1 to 40% or more preferably of about 1 to 35% such as preferably 1 to 30%, more preferably 1 to 25%. Obviously, the amount of tackifier in the drug-containing layer may be critical to the solubility of the steroidal hormone in the drug-containing layer. Thus, in still other embodiments of the invention, the tackifier is present in the drug-containing layer in an amount of up to 35%, such as of up to 30%. More preferably, the amount of tackifier is up to 25%, such as up to 20% or 15%, more preferably of up to 10%, 7%, 5% by weight of the drug-containing layer.

It follows that a further particular aspect of the invention relates to a composition for transdermal delivery of Gestodene or an ester thereof, and optionally an estrogen, the composition comprising a drug-containing layer consisting essentially of:

at least one steroidal hormone, such as a gestodene, and one or more pharmaceutically acceptable ingredient(s) and/or carrier(s);

polymer or a mixture of polymers, preferably in an amount of from about 15 to 99% by weight of the drug-containing layer, the polymer is preferebly selected from the group consisting of hydrocarbon polymers, polysiloxanes, poly-acrylates and mixtures thereof, most preferably hydrocarbon polymers (polyisobutylenes, polybutenes, polyisoprenes, polystyrenes, styrene isoprene styrene block polymers, styrene butadiene styrene block polymers and/or mixtures thereof). As mentioned the drug-containing layer has a solubility for Gestodene as mentioned above; and a tackifier in an amount of up to 85% by weight of the drug-containing layer; and optionally an estrogen.

As being said, the drug-containing layer is to be composed of ingredients forming a layer wherein the solubility criterion for Gestodene is met. Preferably, this criterion is met when the drug-containing layer is mainly composed of the hormones of the invention together with a polymer or a mixture of polymers and optionally a tackifier.

In some embodiments, it is found that a suitable polymer of the invention is lipophilic and essentially without any presence of free hydrophilic groups. Thus, any suitable hydrocarbon polymer, polysiloxane or poly-acrylate is selected from those polymers with a limited amount of functional groups in the side chains, such as free hydrophilic functional groups, such as carboxylic-, ester-, hydroxy-, amino-, amide, halogen- or sulfo-groups. Therefore, in some embodiments, the polymer essentially excludes poly-acrylates, of which some comprise free carboxylic and/or hydroxyl groups.

In preferred embodiments, the polymer is a hydrocarbon polymer, a poly-siloxane or a mixture of the two types of polymers. As mentioned, the hydrocarbon type polymers are of the non-polar type polymers essentially without free hydrophilic functional groups, such as carboxylic-, ester-, hydroxy-, amino-, amide, halogen- or sulfo-groups in the side chains. Therefore, in a most preferred embodiment, the polymer is a hydrocarbon polymer.

A plethora of hydrocarbon polymers exist of both high molecular weight and low molecular weight or mixtures thereof. Typically, the hydrocarbon polymers are in the form of polyisobutylenes, polybutenes, polyisoprenes, polystyrenes, styrene isoprene styrene block polymers, styrene butadiene styrene block polymers or mixtures thereof. The molecular weight of high molecular weight polymers (at least with respect to polyisobutylene) is usually within the range of 500,000 to 2,000,000 Da, whereas that of low molecular weight is of range from about 20,000 to 100,000 Da. Typically, such polymers comprise a mixture of high molecular weight polymers and low molecular weight polymers wherein the amount of the low molecular weight polyisobutylene in the total mixture is at least 50%.

In preferred embodiments, the hydrocarbon polymer is a polyisobutylene, polybutene, polyisoprene, most preferably polyisobutylene.

In some embodiments of the invention the polymer excludes isoprene co-polymers.

The poly-siloxanes are typically high molecular weight polydimethylsiloxanes with free silanol groups or endcapped silanol groups (Bio-PSA®).

Typical examples of poly-acrylates, which as mentioned above may be excluded or used in minimal amounts in some embodiments, include polymers selected from homopolymers of acrylic esters, copolymers of two or more types of acrylic ester units or copolymers of acrylic esters or other functional monomers. Acrylic esters include, but are not limited to, butyl methacrylate, pentyl methacrylate, hexyl methacrylate, heptyl methacrylate, octy methacrylate, nonyl methacrylate, decyl methacrylate. For example ethylene/ethylacrylate copolymers, polymethacrylate polymers and polysiloxane-polymethacrylate copolymers. As mentioned, functional monomers containing a hydrophilic functional group may be excluded as a suitable polymer, such as hydroxyethyl methacrylate, hydroxypropyl methacrylate, etc. and monomers containing an amide group such as methacrylate, dimethylmethacrylamide.

Moreover, for the same reason polymers such as polyalkylenes (polyethylene, polypropylene, ethylene/propylene copolymers, chlorinated polyethylene, polytetrafluoroethylene), polyacetates (ethylene/vinyl acetate copolymers, vinyl chloride-vinyl acetate copolymer), polyvinylenes (polyvinylidene chloride, ethylene-vinyl alcohol copolymer, ethylene-vinyloxyethanol copolymer, polyvinylpyrrolidone) polycarbonates, cellulose polymers (methyl or ethyl cellulose derivatives, hydroxypropyl methyl cellulose and cellulose esters) may not be appropriate polymers according to the invention and are to be excluded or at least used in a restricted amount in some embodiments of the invention. The exclusion does not however prevent the use of such polymers in other layers or parts of the composition.

Furthermore, in some embodiments, the drug-containing layer does not comprise, or at least only comprise a restricted amount of, a hydrophilic polymer, such as crystallisation inhibitors like polyvinylpyrrolidone, cellulose polymers, such as methyl or ethyl cellulose derivatives or hydroxypropyl methyl cellulose, or mixtures thereof.

Also in some embodiments a solubiliser, such as dimethylisosorbide, is not present in the drug-containing layer of at least only present in a restricted amount.

By the term "restricted amount" is meant that the polymer or solubiliser in question is present in a concentration in the drug-containing layer of less than 10%, such as less than 8, 5, 3, 2, 1, 0.5 or 0.2% by weight of the layer.

As mentioned, it has been possible to provide sufficient skin penetration of a steroidal hormone without incorporating a skin penetration enhancer and/or permeation enhancer. That is to say that in interesting embodiments of the invention, a skin penetration enhancer and/or permeation enhancer is excluded in the drug-containing layer or present in the drug-containing layer in a restricted amount, this amount being less than 5%, such as less than 4%, 3%, 2%, 1%, 0.5%, or 0.2% by weight of the drug-containing layer.

The terms "skin penetration enhancers" and "permeation enhancers" are in the present invention meant to be interchangeable terms and denotes compounds, which provide enhanced skin penetration/permeation to the active drugs when it is administered together with the drugs to the skin of a user. Penetration/permeation enhancers in transdermal formulations will change the thermodynamic activity of the drug in the drug-containing layer, and thereby lead to a positive or negative "push" effect. In addition, some penetration/permeation enhancers may conceivably penetrate into the highly ordered intercellular lipid structure of the stratum corneum and reduce its resistance by increasing lipid acyl chain mobility, thus providing a "pull" effect.

Any skin penetrating/permeation enhancing effect of a substance may be recognised upon testing identical formulations with and without penetration enhancer, for example by using nude mouse skin or the like. The skilled person knows such test methods.

Typical penetration/permeation enhancers are included in the group of compound listed below:

Alcohols, such as monohydric alcohols having about 2 to 10 carbon atoms, such as ethyl, isopropyl, butyl, pentyl, octanyl decanyl and/or benzyl alcohols; dihydric alcohols such as 1,2-propanediol polyhydric alcohols such as glycerin, sorbitol and/or polyethylene glycol; saturated and unsaturated fatty alcohols with 8-18 carbon atoms, such as capryl-, decyl-, lauryl-, 2-lauryl-, myristyl-, cetyl-, stearyl-, oleyl-, linoeyl- and linolenylalcohol.

Fatty acids, such as saturated or unsaturated fatty acids that may include 8-18 carbon atoms, for example, lauric acid, myristic acid, stearic acid, oleic acid, linoleic acid, linolenacid and palmitic acid, triacetin, ascorbic acid, panthenol, butylated hydroxytoluene, tocopherol, tocopherol acetate, tocopheryl linoleate. Other fatty acids include but are not limited to valerian acid, capronic acid, capryl acid, pelargon acid, caprin acid, isovalerian acid, neopentan acid, neoheptan acid and/or isostearin acid.

Esters such as aliphatic esters ethyl acetate, lower (C1-C4) alkyl ester of lactic acid, fatty acid esters of the general formula $CH_3-(CH_2)_n-COOR$, wherein n is a number from 8 to 18 and R is an alkyl residue of maximally 6 carbon atoms, such as fatty acid esters for example, those of lauric acid, myristic acid, stearic acid and palmitic acid, e.g., the methyl esters, ethyl esters, propyl esters, isopropyl esters, butyl esters, sec-butyl esters, isobutyl esters of these acids, or dicarboxylic acid diesters of the general formula $R'OCO(CH_2)_m COOR'$, wherein m is a number from 4 to 8 and R' in each case means an alkyl residue of maximally 6 carbon atoms, such as propyl oleate, decyl oleate, isopropyl palmitate, glycol palmitate, glycol laurate, dodecyl myristate, isopropyl myristate and glycol stearate, suitable dicarboxylic acid diesters are, for example, the diisopropyl adipate, diisobutyl adipate and diisopropyl sebacate.

Ethers, such as polyethylene glycol ethers of aliphatic alcohols (such as cetyl, lauryl, oleyl and stearyl) including polyoxyethylene (4) lauryl ether, polyoxyethylene (2) oleyl ether and polyoxyethylene (10) oleyl ether.

Alkanes, such as alkanes with chain lengths of 6 to 17 carbon atoms.

Amides such as dimethyl acetamide, dimethyl formamide, dimethyl lauramide, dimethyl laurylamide and/or fatty acid amides and theirs derivatives.

Amides, such as amides with long aliphatic chains, or aromatic amides, urea and urea derivatives such as cyclic urea, dodecyl-urea, diphenyl-urea and/or allantoin.

Amino acids.

Amino acetates, such as derivatives of amino acetates such as dodecyl-N,N-dimethylaminoacetate and dodecyl-2-methyl-2-(N,N-methylaminoacetate), decyl-2-(N,N-dimethylamino)-propionat, decyl-2-(N,N-dimethylamino)-butyrat, octyl-2-(N,N-dimethylamino)-propionat, and/or docecyl-(N, N-dimethylaminophenylacetate.

Azone derivatives such as 1-dodecylazacycloheptane-2-one derivatives, azacycloalkanone derivatives and/or hexamethylenlauramid derivatives.

Cyclodextrins such as alpha, beta, and gamma cyclodextrins.

Glycerides, such as Monoglycerides, including glycerol monooleate, glycerol monolaurate and glycerol monolinoleate, polyethylene glycol-3-lauramide (PEG LR), polyethylene glycol monolaurate (PGML) glycerol monooleate (GMO), glycerol monolinoleate and/or glycerol monolaurate (GML).

Glycols such as ethylene glycol, diethylene glycol, or propylene glycol dipropylene glycol and/or trimethylene glycol.

Oils, such as mineral, vegetable, animal and fish fats and oils such as cotton seed, corn, safflower, olive and castor oils, squalene, and/or lanolin.

Polyols such as propylen glycol.

Pyrrolidones such as 2-pyrrolidone, N-methyl-2-pyrrolidone, dodecyl-pyrrolidone, 2-pyrrolidon-5-carboxylicacid, N-hexyl-, N-lauryl-, 4-carboxy-, 4-carboxycarbon derivatives, 3-hydroxy-N-methyl-2-pyrrolidon, N-farnesyl-2-pyrrolidon, N-(2(decylthio)ethyl)-2-pyrrolidone and/or N-(2-hydroxyethyl)-2-pyrrolidone.

Sulfoxides such as sulfoxide derivatives such as methyloctyl-sulfoxide, dimethyl-sulfoxide (DMSO), hexylmethyl-sulfoxide (hexyl-MSO) and/or decylmethyl-sulfoxide (decyl-MSO).

Surface active agents such as cationic surfactants like cetyltrimethylammonium bromide, octadecyltrimethylammoniumchloride, cetylpyridiniumchloride and/or equivalent cationic compounds, anionic surfactants such as sulphate salts which include but are not limited to compounds such as sodium lauryl sulphate and/or sodium dodecyl sulphate, and non-ionic surfactants such as esters of sorbitol and sorbitol anhydride which include but are not limited to polysorbate, sorbitan-monopalmiate and/or sorbitan-polyoleat.

Terpenes, ketones and oxides.

In addition to the steroidal hormone, such as a progestin, the one or more polymers, the one or more tackifiers and the optional estrogen, the drug-containing layer or other parts of the composition also contain stabilisers, dyes, pigments, inert fillers, anti-ageing agents, anti-oxidants, elastomers, thermoplastics and other conventional components of transdermal compositions that are known in the art. Preferably, the composition, or at least the drug-containing layer, does not comprise or does only comprise in a restricted amount (less than 1%, 0.8%, 0.5%, 0.2% or 0.1% by weight of the drug-containing layer) polyvinylpyrrolidone, methylcellulose, ethyl cellulose, hydroxypropyl methylcellulose, and/or dimethylisosorbide.

It should be understood that compositions of the inventions are transparent or at least in very interesting embodiments transparent, which means that the skin can be visually inspected through the drug delivery system. That is to say that the drug-containing layer is a monophasic system in which the drug (here progestin) is completely dissolved in the drug-containing layer. The property as a monophasic system may be identified by mechanical stretching of the drug-containing layer by using a test method as described below.

The drug-containing layer is further characterised by being homogenous. The term "homogeneous" is used to describe a monophasic system, wherein the matrix is composed of one polymer phase. These systems can be distinguished from multiphasic systems, which are composed of at least two polymer phases. In most cases multiphasic systems can be detected visually by their opaque appearance. The opaque appearance is caused by the light diffraction due to differences in the diffraction index of the polymer phases. Other methods to detect monophasic systems are microscopic or rheological methods or by mechanical streching thin polymer films. During mechanical stretching the thin polymer film composed of multiphasic systems turns opaque, as determined visually.

Thus, in summary it should be understood that interesting embodiments of the invention include:

a drug-containing layer that comprises:
  i) a progestin such as Gestodene or an ester thereof; and
  ii) a polymer selected from the group consisting of polyisobutylenes, polybutenes, polyisoprenes, polystyrenes, styrene isoprene styrene block polymers, styrene butadiene styrene block polymers and mixtures thereof.

In further interesting embodiments thereof the drug-containing layer is characterised by the following parameters, which may be present as a single parameter or as mixture of parameters;

The drug-containing layer has a solubility for Gestodene of no more than 3% by weight of the drug-containing layer;

The drug-containing layer excludes dimethylisosorbide or contains an amount of dimethylisosorbide of less than 0.5% by weight of the layer;

The drug-containing layer excludes polyvinylpyrrolidone, methylcellulose, ethylcellulose and/or hydroxypropylcellulose or contains an amount of less than 2% of polyvinylpyrrolidone, methylcellulose, ethylcellulose and/or hydroxypropylcellulose by weight of the layer;

The drug-containing layer contains the progestin (Gestodene or an ester thereof) completely dissolved in the layer;

The drug-containing layer comprises the Gestodene or an ester thereof in an amount of 0.5-3% by weight of the drug-containing layer;

The drug-containing layer is transparent;

The drug-containing layer is homogenous;

The drug-containing layer is monophasic;

The drug-containing layer excludes a skin penetration enhancer or contains an amount of less than 2% by weight of the layer;

The drug-containing layer comprises said polymer in an amount of from about 15 to 99% by weight of the layer;

The drug-containing layer comprises a tackifier, such as a rosin ester, in an amount of up to 85% by weight of the drug-containing layer;

As mentioned above, the compositions of the invention are characterised by delivering an effective contraceptive amount of a steroidal hormone, such as a progestin, such as a gestodene, optionally in combination with an estrogen. In the embodiment, wherein the progestin is Gestodene or a derivative thereof the composition may be characterised by providing an in-vitro nude mouse skin permeation rate of Gestodene and/or a derivative thereof of at least 25 µg/cm$^2$*24 h. In other terms, the composition may be characterised by having a drug-containing layer delivering Gestodene and/or a derivative thereof in an amount of from about 40 to 70 µg per day.

Not only Gestodene or a derivative thereof may be used as a drug in the composition of the invention. Other progestins may be included in the drug-containing layer together with Gestodene or in place of a gestodene, such as dienogest, drospirenone, levornorgestrel, cyproteronacetate, tetrahydrodienogest, norethisterone, norethisteronacetate, desogestrel, 3-keto-desorgestrel, norgestimate, lynestrenol, medroxyprogesteroneacetate, norgestrel, norethisteroneenanthate, trimegestone or alpha and beta-progesterone receptor ligands.

As mentioned, the composition is effective in inhibiting ovulation. In some instances, the composition further comprises an estrogen. The estrogen may be incorporated together with the progestin in the same drug-containing layer or be incorporated in a separate drug-containing layer free of the progestin.

The term "estrogen" includes both the natural 17β-estradiol and the semi-synthetic estrogen derivatives such as esters of natural estrogen and 17-alkylated estrogens. Semi-synthetic esters of natural estrogen include for example estradiol-17-β-enanthate, estradiol-17-β-valerate, estradiol-17-β-benzoate, estradiol-17-β-undecanoate, estradiol-16,17-hemisuccinate or estradiol-17-β-cypionate. Examples on 17-alkylated estrogens are Ethinylestradiol, Ethinylestradiol-3-isopropylsulphonate, quinestrol, mestranol or methyl estradiol. The term "estrogen" may also include a non-steroidal compound having estrogen activity, such as diethylstilbestrol, dienestrol, clomifen, chlorotrianesene or cyclofenil.

In a preferred embodiment, the estrogen is Ethinylestradiol.

To achieve the therapeutically effective amount of hormone in the blood, the actual concentration of the drug in the drug-containing layer may be adjusted. Generally speaking, the drug-containing layer should contain some hormone in excess of the amount of hormone to be absorbed for achieving the therapeutically effective amount of the hormone. Normally, this excess is small, such as the amount of hormone is less than 10 times the desired/required amount of hormone, preferably less than 5 fold, such as less than 2 fold. For example, it is also considered important to limit the amount of hormone so as to reduce the overall exposure of hormone to the user. Appropriate concentrations of a steroidal hormone, such as a progestine, such as Gestodene or a derivative thereof, in the drug-containing layer is therefore from about 0.5 to 10% by weight of the drug-containing layer. In still more preferred embodiments, the concentration of said hormone is about 0.5 to 10%, such as from about 0.75 to 5%. "As mentioned, the total concentration of hormone, such as Gestodene may result in drug-containing layers comprising the hormone in saturated or sub-saturated levels. In a very interesting embodiment, the concentration of a steroidal hormone, such as Gestodene or a derivative thereof, in the drug-containing layer is from about 1 to 3%, such as 1 to 2%.

Likewise, in some embodiments of the invention that further comprise an estrogen, the estrogen is present in the drug-containing layer in an amount of from about 0.5 to 10% by weight of the adhesive layer, preferably of from about 0.75 to 5%, more preferably of from about 1 to 3%, such as 1 to 2%.

Moreover, the said progestin, such as Gestodene or a derivative thereof is in a mass ratio to said estrogen in the range of from about 4 to 0.5, preferably 2 to 0.5 such as 1:1.

It has surprisingly been found that relatively high plasma levels of Gestodene can be maintained for a prolonged period of time by administering Gestodene or a derivative thereof formulated in a composition of the invention. Also surprisingly, it is found that the plasma profile and plasma levels of Gestodene, as resulting from the administration of Gestodene or a derivative thereof and optionally an estrogen, are effective in inhibiting the ovulation in a woman.

Therefore, further aspects of the invention relate to the use of a composition of the invention, optionally in combination with an estrogen, for the inhibition of ovulation in a female, such as a woman. When the medicament is singly administered, then a plasma concentration-time curve of Gestodene is achieved characterised by having plasma levels of Gestodene in a concentration of at least 1.0 ng/ml, as determined at steady state conditions. As follows, an aspect of the invention relates to a method for inhibiting ovulation in a female, such as a woman, comprising administering topically to skin or mucosa an effective amount of Gestodene or a derivative thereof, optionally in combination with an estrogen, so as upon singly administering said gestodene, then a plasma concentration-time curve of Gestodene is achieved characterised by having plasma levels of Gestodene in a concentration of at least 1.0 ng/ml, as determined at steady state conditions.

Alternatively, the uses and methods of the invention are for the treatment of other symptoms, disorders or symptoms which are normally treated by administering a progestin, such as Gestodene or a derivative thereof or a combination of a progestin and an estrogen.

Therefore, it should in general be understood that in some embodiments of the invention, the uses and methods are for the treatment of endometriosis, pre-menstrual syndrome, climacteric disorders, regulating menstrual cycle and/or stabilising menstrual cycle.

For example, administering a progestin without concurrent therapy with an estrogen can treat irregular bleeding and abnormal bleeding. As used herein, the term "irregular bleeding" characterises any uterine bleeding, outside the regular monthly menstrual periods of non-pregnant women. Uterine bleeding are irregular if menstrual cycles or menstrual periods are too short, too long, too frequent, too infrequent, or occur at irregular intervals which falls outside the regular 26-30 days menstrual cycle. The menstrual period is classified as too long when being delayed with 15 to 50 days or more to the expected onset of said bleeding. The term "abnormal bleeding" characterises heavy bleeding typically soaking through enough sanitary protection products to require changing more than every one or two hours, having a period that lasts over seven days. Abnormal bleeding does not include bleeding in women who have already reached menopause, abnormal uterine bleeding due to side effects of estrogen replacement therapy, abnormal bleeding as a symptom of uterine cancer, as a result of a consequence of abnormal blood clotting normally, an inherited bleeding disorder or because of a medical illness that affects levels of blood platelets.

In other embodiments, the progestin is administered in combination with an estrogen, such as by administering a medicament of the invention comprising the combination of a progestin, such as Gestodene or a derivative thereof, and an estrogen for the treatment of climacteric disorders, such as symptoms and diseases associated with meno-pause, such as hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition and/or osteoporosis. Most notably the treatment is directed to hot flushes, sweating attacks, palpitations, sleep disorders, mood changes, nervousness, anxiety, urogenital atrophy, atrophy of the breasts or for the prevention or management of osteoporosis.

In connection with treatment of climacteric disorders, the estrogen may be selected from natural estrogens, such as estradiol and esters thereof, such as estradiol valerate, estradiol benzoate. Furthermore, natural estrogens include estrone, estriol, estriol succinate and conjugated estrogens, including conjugated equine estrogens such as estrone sulfate, 17β-estradiol sulfate, 17α-estradiol sulfate, equilin sulfate, 17β-dihydroequilin sulfate, 17α-dihydroequilin sulfate, equilenin sulfate, 17β-dihydroequilenin sulfate and 17α-dihydroequilenin sulfate or mixtures thereof.

In some embodiments of the invention, the plasma concentration-time curve of Gestodene at steady state conditions is characterised by having plasma levels of Gestodene in a concentration of at least 1.5 ng/ml, such as at least 2.0 ng/ml or at least 2.5 ng/ml. In other interesting embodiments, the plasma concentration-time curve of Gestodene at steady state conditions is characterised by having plasma levels of Gestodene in the range of 1 to 8 ng/ml, preferably in the range of 1.5 to 6 ng/ml following the first 6 days after single administration of a composition of Gestodene or a derivative thereof, preferably in the form of a composition of the invention.

In still further embodiments, the plasma concentration-time curve of Gestodene at steady state conditions is characterised by having maximal plasma levels of Gestodene in the period of 18 to 60 hours following single administration of the medicament and/or having plasma levels of Gestodene at steady state conditions in the period of 5 to 7 days following single administration of the medicament in the order of at least 50% of the maximal plasma levels of Gestodene obtained during the first 18 to 60 hours following administration.

The gestodene is preferably administered repeatedly in cycles of 28 days such that within each cycle of 28 days, the gestodene/composition is administered with an interval of 7 days in a period of 21 days (3 weeks) followed by no administration of Gestodene or a derivative thereof for 7 days (one week). That is to say that the gestodene/composition is administered on day 1, 8 and 15 within each cycle of 28 days. Preferably, said day 1 may be the day of the start of menstruation, or any other suitable day, such as the first, second, third, fourth, fifth or sixth day following the day of start of menstruation. In another embodiment, the gestodene, optionally in combination with an estrogen, is administered repeatedly in cycles of 12 weeks such that within each cycle of 12 days, the gestodene/composition is administered with an interval of 7 days in a continuous period of 11 weeks followed by no administration of Gestodene or a derivative thereof for 7 days (one week).

To improve the contraceptive efficacy and security, an estrogen may be administered concomitantly with the gestodene. The estrogen may be selected from the estrogens mentioned above.

As may be understood, the uses and methods of the invention include the application of Gestodene or a derivative thereof, which may be in the form of a composition as defined herein. Thus, the term "medicament" includes a composition as defined herein. Furthermore, the term "medicament" is meant to include a kit of the invention.

In a still further aspect, the invention relates to a kit comprising 1 to 11 dosage units intended for a treatment period of 12 weeks formulated in a form for transdermal delivery of a progestin, such as of Gestodene or a derivative thereof, said dosage units comprise a drug-containing layer comprising gestodene and one or more pharmaceutically acceptable excipients or carriers and the drug-containing layer has a solubility with respect to said gestodene of no more than 3% by weight of the drug-containing layer. The dosage unit may comprise a composition as described herein. It is to be understood that in one embodiment thereof, 11 dosage units are administered continuously once weekly during a period of 11 weeks followed by one week of no administration of a dosage unit or administration of a placebo.

In other embodiments, the kit is intended for a treatment period of 12 weeks, but the kit comprises 1 to 9 dosage units. In one embodiment, 3-dosage units are administered weekly for a period of 3 weeks, followed by one week of no administration of a dosage unit or administration of a placebo. That is to say that the kit is intended for a treatment period of 4 weeks and the kit comprises 1-3 dosage units.

The dose of the progestin, such as of Gestodene or a derivative thereof in each dosage unit corresponds to a dose selected from a 6-day dose, 7-day dose, 8 day-dose, 14-day dose or 21-day dose. In one embodiment thereof, each dosage unit comprises Gestodene or a derivative thereof in a dose from about 0.5 to 5 mg, preferably 1 to 3 mg, more preferably 1.5 to 2.5 mg.

It is further to be understood that the kit may further comprise an estrogen as mentioned above. The estrogen may be combined together with the progestin, such as Gestodene or a derivative thereof, in the same dosage unit or provided in separate dosage units. The kit may for example further comprises 1 to 30 dosage units comprising an estrogen and no gestodene. The estrogen may be in a dosage form formulated for transdermal delivery, vaginal delivery or the like. Alternatively, the estrogen may be in the form of dosage units formulated for peroral delivery of an estrogen, such as in the form of a tablet, pill, capsule, powder, paste or granules.

The compositions of the invention may be fabricated using procedures known in the art. One example is included herein.

FIGURES

FIG. 1. Mean serum levels of Gestodene (GSD) during two treatment cycles, week 1 and week 3, respectively. The legends are as follows:
cycle 1, week 1
cycle 2, week 1
cycle 1, week 2 week 3
A cycle 2, week 2 week 3

EXAMPLES

Example 1

Manufacturing Of A Patch

A composition of the invention is prepared as follows.

In a first step 380 g of Gestodene, and optionally 180 g of Ethinylestradiol, is dissolved in an appropriate solvent, such as 16.8 kg of dioxane. In a second step, about 57 kg of a mixture of polyisobutylene and rosin ester in heptane (Arcare® MA 24A) is weighed off. The hormone solution of the first step is transferred under stirring to the polymer solution and stirring is continued until a homogeneous solution is achieved. The thus obtained drug-containing solution is coated onto a release liner (such as FL 2000 75 µm PET 1S; Fa Loparex) and dried under appropriate conditions. The dried drug-containing layer is then laminated with a backing foil/layer, such as Cotran®, 9720, 3M. The thus obtained laminate is divided into patches of the size of 10 cm$^2$ and the resulting patch has the following composition:

| | |
|---|---|
| Gestodene: | 1.9 mg |
| Optionally Ethinylestradiol: | 0.9 mg |
| Polymer | 97.2 mg |
| (in the form of polyisobutylene in combination with a tackifier e.g MA-24A ®) | |
| Release liner: | 10 cm$^2$ |
| Backing layer: | 10 cm$^2$ |

In another example, the resulting patch is similar to the above-mentioned but the amount of Ethinylestradiol is 0.6 mg.

In still another example, the resulting patch is similar to the above-mentioned but the adhesive is Duro-tak®, 10711, which is composed of a hydrocarbon polymer.

Example 2

Skin Penetration Rates Of Compositions With Various Polymers Six compositions (A-F) were manufactured with acrylate-vinylacetate polymers as the polymer in the drug-containing layer. Furthermore, composition G was made using polyisobutylene as the polymer in the drug-containing layer. The manufacturing was performed according to the process as described in Example 1. None of the compositions comprises a skin penetration enhancer.

Each of the compositions were tested in the in-vitro mouse skin permeation test. The test is performed using skin preparations of nude mouse skin (HsdCpb: NMRI-nu) available from Harlan Bioservice for Science GmbH, Walsrode, Germany. The test formulation is attached on the outside of a skin specimen. Both are placed into the permeation cell with the inside in contact with the receptor media. HEPES buffered aqueous solution is used as receptor media. Sodium azide is added to prevent microbial growth. The receptor solution is maintained at 32° C. Samples are taken from the receptor solution at defined time intervals and the concentration of Gestodene (GSD) and Ethinylestradiol (EE) in the receptor media were analysed by HPLC. The flux rate was then calculated as the amount of drug released per area and time unit [$\mu g/cm^2 * 24\ h$] using the calculated amounts of active substances.

Results on skin penetration rate in vitro:

the selected women were ovulatory. Finally, the second phase is a treatment phase of two cycles, which was followed by a third phase consisting of one-cycle post-treatment phase.

Women enrolled in the study were required to be healthy, non-pregnant, non-smoking, non-lactating female volunteers aged between 18 and 35 years, with a normal body mass index of 18-26 $kg/m^2$ and a normal menstrual cycle length such as 28 days±4 days. Only women with light skin were included so that application sites could be easily and uniformly assessed.

The test patch is a patch comprising a drug-containing layer of 0.9 mg Ethinylestradiol and 1.9 mg Gestodene and Arcare MA-24A®, the drug containing layer has a size of 10 $cm^2$. Arcare MA-24A® is a polyisobutylene based adhesive from Adhesive Research.

During the study, blood was drawn for the determination of endogenous hormones, such as estradiol, progesterone, follicle stimulating hormone, sex hormone binding proteine, Ethinylestradiol, Gestodene. Transvaginal ultrasound examination were carried out to evaluate development of ovarian follicle-like structures. Patch adhesion, skin reactions at the application site and the woman's general health status was assessed. Vaginal bleeding was also evaluated.

During the pre-treatment cycle normal and spontaneous ovulation was established by assessment of serum progesterone values in that only women with an ovulatory pre-cycle and progesterone serum levels higher than 5 nmol/l were admitted to the treatment phase.

The treatment phase includes a period of two menstrual cycles. The first treatment in the first cycle began one day after the volunteers started menstruating in this cycle by applica-

TABLE 1

| | Formulation | | | | | | |
|---|---|---|---|---|---|---|---|
| | A | B | C | D | E | F | G |
| GSD (% w/w) | 1.9 | 3.9 | 2.1 | 4.2 | 1.9 | 3.8 | 1.9 |
| EE (% w/w) | 1.0 | 2.0 | 1.1 | 2.1 | 1.0 | 1.9 | 0.9 |
| Polymer | Acrylate-vinylacetate e.g. Durotak® 387-2051 | Acrylate-vinylacetate e.g. Durotak® 387-2051 | Acrylate-vinylacetate e.g. Durotak 387-2825 | Acrylate-vinylacetate e.g. Durotak 387-2825 | Acrylate-vinylacetate e.g. Durotak 87-2097 | Acrylate-vinylacetate e.g. Durotak 87-2097 | PIB e.g. MA-24A |
| GSD permeation $\mu g/cm^2 * 24\ h$ | 14.8 | 32.8 | 12.6 | 14.3 | 13.5 | 16.7 | 30.9 |
| EE permeation $\mu g/cm^2 * 24\ h$ | 2.6 | 6.5 | 1.5 | 2.8 | 1.3 | 1.9 | 8.1 |

The results indicate that the permeation rate of Gestodene as well as of Ethinylestradiol from composition G (polyisobutylene) is superior to that from compositions A-F.

Example 3

Contraceptive Effect and Pharmacokinetic Profile

The effect on ovulation inhibition, serum drug concentrations and safety of a patch of the invention was investigated in a selected population of women. The study design was based on the requirements of the EMEA guideline for clinical studies with contraceptive steroids (Commitee for Proprietary Medicinal Products, CPMP/EWP 519/98).

Study Design

The study has three phases; a pre-treatment phase including two washout cycles and one additional cycle to ensure that tion of a patch. A total of three test patches were applied in intervals of 7 days between, such as application at days 1, 8 and 15 of the first cycle—each at different application sites—during each treatment cycle. Each patch was worn for 7 days, then replaced with a new patch to complete a total of 21 days of continuous use. This was followed by a 7-day treatment-free interval before the next treatment period started with a total of three patches applied, each applied with an interval of 7 days. If the patches were lost or became more than 40% detached, a new patch was applied.

Patches were applied to the clean, dry intact and preferably hairless skin of the lower abdomen, below the navel, starting with the right side in the first treatment cycle, then alternating sides.

Determination of Pharmacodynamic Variables

The primary pharmacodynamic variable is the proportion of women with ovulation inhibited. In accordance with the so-called Hoogland method, ovulation requires follicular growth beyond 13 mm and subsequent ovarian rupture, plus a serum progesterone concentration >5 nmol/l that concurs with the follicle rupture. As follows, the ovulation is said to be inhibited when the follicle is below 13 mm and the serum progesterone concentration is below 5 nmol/l at the time of follicle rupture.

Determination of Pharmacokinetic Variables

Pharmacokinetic parameters such as area under the drug concentration time curve during the patch-wearing period $AUC_{(0-168h)}$, $C_{max}$, $t_{max}$, and accumulation factors within each cycle, such as determined by the $AUC_{(0-168h)}$ of 3 rd patch/$AUC_{(0-168h)}$ of 1 st patch within cycle 1 or 2, or accumulation factors between two cycles, such as $AUC_{(0-168h)}$ of 3 rd patch in cycle 2/$AUC_{(0-168h)}$ of 3rd patch in cycle 1. The AUC was calculated according to the linear trapezoidal rule.

Serum concentrations of the estrogen and progestin, including Ethinylestradiol and Gestodene, were determined throughout the study to assess the pharmacokinetic characteristics of the patch. The sampling points were at the day 18 of the last pre-treatment cycle and days 1, 2, 3, 4, 5, 6, 7, 8, 15, 16, 17, 18, 19, 20, 21 and 22 of cycle 1 as well as days 1 (before application of new patch), 2, 3, 4, 5, 6, 7, 8, 15, 16, 17, 18, 19, 20, 21 and 22 of cycle 2.

The concentrations of Ethinylestradiol and Gestodene were determined by conventional methods known in the art. Specifically, the concentration of Ethinylestradiol was determined by gas chromatography using mass spectrometry in the chemical ionisation mode as the detection method following the extraction of Ethinylestradiol from acidified serum and consecutive derivatization. Gestodene concentrations were determined by radioimmunioassay using a rabbit antiserum and 3H-labelled Gestodene. After incubation and centrifugation, the resultant precipitate was redissolved with NaOH. The assay has a lower limit of quantification of approx. 250 µg/ml.

Results

The primary pharmacodynamic variable was the proportion of women with ovulation inhibition.

Ovarian activity was suppressed effectively, i.e.;
No Ovarian Activity: cycle 1: 78%, cycle 2:56%.
Potential Activity: cycle 1: 1$^5$%, cycle 2:22%.
Non-active FLS: cycle 1: 4%, cycle 2: none;
Active FLS: cycle 1: 4%, cycle 2:22%

No cases of ovulation were found throughout the study. Ovulation inhibition, defined as a Hoogland score lower than 6 (ovulation), was sufficient for all volunteers in the per protocol data set throughout the study.

Progesterone concentrations were adequately suppressed below 2.5 nmol/l in each of the treatment cycles. Mean estradiol levels in the blood was under 20 pg/ml on all days on which a patch was applied.

Pharmacokinetic Results

In all predose samples, Ethinylestradiol (EE) and Gestodene (GSD) serum concentrations were below the limit of quantitation (LOQ: 10 pg/ml for EE, 250 pg/ml for GSD). After administering the study medication, EE and GSD serum concentrations were quantifiable for at least 168 hours in all subjects. See results in Table 2 and 3 as well as in FIG. 1.

TABLE 2

Mean pharmacokinetic parameters of ethinyl estradiol (EE)

| Pharmacokinetic parameter | Unit | Cycle 1 Week 1 | Cycle 1 Week 3 | Cycle 2 Week 1 | Cycle 2 Week 3 |
|---|---|---|---|---|---|
| Cmax | pg/ml | 45.6 | 50.4 | 45.2 | 48.0 |
| Tmax | h | 48 | 24 | 48 | 48 |
| AUC(0-168 h) | ng × h/ml | 5.3 | 6.1 | 5.1 | 5.8 |

TABLE 3

Mean pharmacokinetic parameters of gestodene (GSD)

| Pharmacokinetic parameter | Unit | Cycle 1 Week 1 | Cycle 1 Week 3 | Cycle 2 Week 1 | Cycle 2 Week 3 |
|---|---|---|---|---|---|
| Cmax | pg/ml | 1564 | 3896 | 2219 | 4416 |
| Tmax | h | 144 | 48 | 96 | 48 |
| AUC(0-168 h) | ng × h/ml | 194 | 524 | 302 | 598 |

Example 4

Comparison of Polyisobutylene Adhesive and Acrylic Formulation in Human

A randomized, cross-over study to determine the average daily delivery of Ethinylestradiol (EE) and gestodene (GSD) from three different transdermal patch formulations (A-C) in healthy postmenopausal volunteers following single administration was carried out. The aim was also to compare the transdermal application with that of intravenous injection.

The test formulations were as follows:

Formulation A (Polyisobutylene)

| No. | Name of ingredient | Amount per 10 cm² patch | Remark |
|---|---|---|---|
| 1 | Ethinylestradiol | 0.95 mg | |
| 2 | Gestodene | 1.9 mg | |
| 3 | Polyisobutylene Adhesive | 97.15 mg | MA-24A |

Formulation B (Polyisobutylene, 70% of Formulation A)

| No. | Name of ingredient | Amount per 10 cm² patch | Remark |
|---|---|---|---|
| 1 | Ethinylestradiol | 0.67 mg | |
| 2 | Gestodene | 1.33 mg | |
| 3 | Polyisobutylene Adhesive | 98.00 mg | MA-24A |

Formulation C (Acrylate)

| No. | Name of ingredient | Amount per 10 cm² patch | Remark |
|---|---|---|---|
| 1 | Ethinylestradiol | 0.67 mg | |
| 2 | Gestodene | 1.33 mg | |
| 3 | Acrylic Adhesive | 73.5 mg | Gelva ® 7883 |
| 4 | Isopropyl myristate | 5.0 mg | Permeability enhancer |

-continued

Formulation C (Acrylate)

| No. | Name of ingredient | Amount per 10 cm² patch | Remark |
|---|---|---|---|
| 5 | Copovidone | 15.0 mg | Crystalization inhibitor (Kollidon VA64, BASF, Germany) |

The study was carried out according to the following parameters:

The patches were administered by single transdermal administration with a 7-day wearing period per test. One week of washout was carried out after removal of patch at each test treatment. A dose of 60 µg EE and 75 µg of GSD was administered intravenously once.

Blood sampling for kinetic measurements was at 72 hours after intravenous administration and during a period of 12 days after transdermal administration as described in Example 3. Determination of blood levels of GSD and EE were carried out according to Example 3.

Results

The maximum concentrations of gestodene are given in the following table indicating the difference of the polyisobutylene formulations A and B and the acrylic formulation. The FIGURE shows the time course of the gestodene mean serum levels.

| Parameter | Formulation A | Formulation B | Formulation C |
|---|---|---|---|
| $C_{max}$ [pg/ml]: | 2082 | 1995 | 1277 |
| $t_{max}$ [h]: | 168 | 144 | 156 |
| AUC (0-7d): [h * ng/mL] | 243 | 257 | 155 |

The results indicate that the drug delivery of Formulation C, which included a drug-containing layer of an acrylate in combination with a penetration enhancer, is significantly lower than the drug delivery from Formulations A and B.

Example 5

Drug-containing layers containing 1.9 mg of Gestodene and 0.9 mg of Ethinylestradiol and composed of different mixtures of polymers are shown (A to M).

| Polymer Brand name | Polymer Chemical name | A | B | C | D | E | F | G |
|---|---|---|---|---|---|---|---|---|
| Foral 85E ® | Pentaerythritol ester of hydrogenated rosin | 20.0 | | | | | | |
| Foral 105E ® | Glycerol ester of hydrogenated rosin | | 20.0 | | | | 30.0 | |
| Oppanol B10 N/SFN ® | Polyisobutylene (MW about 40.000 Daltons) | 57.2 | 57.2 | | | 67.2 | 55.2 | |
| Oppanol B11 SFN ® | Polyisobutylene (MW about 49.000) | | | | | | | 62.2 |
| Oppanol B12 SFN ® | Polyisobutylene (MW about 55.000 dalton) | | | 62.2 | 62.2 | | | |
| Oppanol B30 SFN ® | Polyisobutylene (MW about 200.000 dalton) | | | | | | | |
| Oppanol B100 | Polyisobutylene (MW about 1.000.000 Dalton) | 20.0 | 20.0 | 12.0 | 12.0 | 20.0 | 12.0 | 15.0 |
| Oppanol B150 | Polyisobutylene (MW about 2.600.000 Dalton) | | | | | | | |
| Indopol H300 | Synthetic Polybutene (MW about 1.300 Dalton) | | | | | 10.0 | | |
| Indopol H1900 | Synthetic Polybutene (MW about 2.500 Dalton) | | | 23.0 | | | | |
| Indopol H2100 | Synthetic Polybutene (MW about 2.500 Dalton) | | | | 23.0 | | | |
| Escorez 5300 | cyclic aliphatic petroleum hydrocarbon resin | | | | | | | 20.0 |
| Staybelite Ester 3E | Ester of Hydrogenated Resin | | | | | | | |
| Staybelite Ester 5E JQ | glycerol ester of partially hydrogenated rosin | | | | | | | |
| Kraton D1161NU | styrene-isoprene-styrene block polymer | | | | | | | |

| Polymer Brand name | Polymer Chemical name | H | I | J | K | L | M |
|---|---|---|---|---|---|---|---|
| Foral 85E ® | Pentaerythritol ester of hydrogenated rosin | 10.0 | | | | | |
| Foral 105E ® | Glycerol ester of hydrogenated rosin | | 10.0 | | | | 65.0 |
| Oppanol B10 N/SFN ® | Polyisobutylene (MW about 40.000 Daltons) | 67.2 | 67.2 | | 75.7 | 75.7 | |
| Oppanol B11 SFN ® | Polyisobutylene (MW about 49.000) | | | | | | |
| Oppanol B12 SFN ® | Polyisobutylene (MW about 55.000 dalton) | | | 57.2 | | | |

| Component | Description | | | | | |
|---|---|---|---|---|---|---|
| Oppanol B30 SFN ® | Polyisobutylene (MW about 200.000 dalton) | 10.0 | 10.0 | | | |
| Oppanol B100 | Polyisobutylene (MW about 1.000.000 Dalton) | 10.0 | 10.0 | 15.0 | | |
| Oppanol B150 | Polyisobutylene (MW about 2.600.000 Dalton) | | | | 10.8 | 10.8 |
| Indopol H300 | Synthetic Polybutene (MW about 1.300 Dalton) | | | | | |
| Indopol H1900 | Synthetic Polybutene (MW about 2.500 Dalton) | | | | | |
| Indopol H2100 | Synthetic Polybutene (MW about 2.500 Dalton) | | | | | |
| Escorez 5300 | cyclic aliphatic petroleum hydrocarbon resin | | | | | |
| Staybelite Ester 3E | Ester of Hydrogenated Resin | | | | 10.8 | |
| Staybelite Ester 5E JQ | glycerol ester of partially hydrogenated rosin | | | 25.0 | | 10.8 |
| Kraton D1161NU | styrene-isoprene-styrene block polymer | | | | | | 32.2 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding U.S. Provisional Application Ser. No. 60/528,718, filed Dec. 12, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A composition for transdermal delivery comprising a drug-containing layer wherein the drug-containing layer consists essentially of Gestodene or an ester thereof, ethinyl estradiol and at least one pharmaceutically acceptable earner which comprises a polyisobutylene polymer, one or more tackifiers selected from the group consisting of hydrocarbon resins, rosin resins and terpene resins and optionally a polybutene polymer, and wherein the drug-containing layer contains 25% to 99% by weight of polyisobutylene polymer(s) including at least one polyisobutylene polymer with a high molecular weight of about 500,000 to 2,000,000 Da and at least one polyisobutylene polymer with a low molecular weight of about 20,000 to 100,000 Da, wherein the drug-containing layer has a solubility for said Gestodene or an ester thereof of no more than 3% by weight of the drug-containing layer and the Gestodene or an ester thereof is completely dissolved in the layer, wherein the Gestodene or an ester thereof is in an amount ranging between 0.5 and 3% by weight of the drug-containing layer, and wherein the drug-containing layer excludes a skin penetration enhancer.

2. The composition according to claim 1, wherein the tackifier is a rosin ester.

3. The composition according to claim 1, wherein the drug-containing layer is transparent.

4. A kit comprising 1 to 11 dosage units intended for a treatment period of 12 weeks formulated in a form for transdermal delivery of Gestodene or an ester thereof, said dosage unit comprises a composition as defined in claim 1.

5. The kit according to claim 4, wherein the kit is intended for a treatment period of 12 weeks and the kit comprises 9 dosage units.

6. The kit according to claim 4, wherein the kit is intended for a treatment period of 4 weeks and the kit comprises 4 dosage units.

7. The kit according to claim 4, wherein the gestodene is present in an effective dose corresponding to a dose selected from a 6-day dose, 7-day dose, S day-dose, 14-day dose or 21-day dose.

8. The kit according to claim 4, wherein each dosage unit comprises a Gestodene in a dose from about 0.5 to 5 mg.

9. A method for inhibiting ovulation in a female, comprising administering topically to the skin or the mucosa an effective amount of Gestodene or an ester thereof; in combination with ethinyl estradiol, by means of a composition of claim 1, so that after single administration of said Gestodene or an ester thereof, a plasma concentration-time curve of Gestodene is achieved having plasma levels of Gestodene in a concentration of at least 1.0 ng/ml, as determined at steady state conditions.

10. The method according to claim 9, wherein the plasma concentration-time curve of Gestodene achieves plasma levels of Gestodene in the range of 1 to 8 ng/ml following the first 6 days after single administration.

11. The kit according to claim 4, wherein each dosage unit comprises a Gestodene in a dose from about 1 to 3 mg.

12. The kit according to claim 4, wherein each dosage unit comprises a Gestodene in a dose from about 1.5 to 2.5 mg.

13. The composition according to claim 1, wherein: the composition contains the Gestodene in the drug-containing layer in a dose of from about 1.5 to 2.5 mg; and the composition is transparent.

14. A kit for a treatment period of 28 days containing four transdermal delivery dosage units, each for a period of 7-day use wherein three of the 7-day use dosage units contain a composition according to claim 13 and the fourth 7-day dosage unit contains a composition with no Gestodene.

15. The composition of claim 13, wherein the drug-containing layer comprises a rosin ester tackifier.

16. The kit of claim 14, wherein the drug-containing layer comprises a rosin ester tackifier.

17. The kit of claim 14, wherein the transdermal dosage units are transparent.

18. The kit of claim 14, wherein the three dosage units with the Gestodene-containing composition comprise a hacking layer, a drug-containing layer with contains the Gestodene-containing composition and a removable release liner.

19. The kit of claim 18, wherein the transdermal dosage units are transparent.

20. The kit of claim 18, wherein the drag-containing layer of the transdermal dosage units have a size of 5 to 20 cm².

21. The kit of claim 19, wherein the drug-containing layer of the transdermal dosage units have a size of 5 to 20 cm².

22. The composition of claim 1, wherein the drug-containing layer contains 25% to 85% by weight of polyisobutylene polymer(s),

* * * * *

UNITED STATES PATENT AND TRADEMARK OFFICE
CERTIFICATE OF CORRECTION

PATENT NO.         : 8,668,925 B2                                        Page 1 of 1
APPLICATION NO.    : 11/008642
DATED              : March 11, 2014
INVENTOR(S)        : Thomas Langguth et al.

It is certified that error appears in the above-identified patent and that said Letters Patent is hereby corrected as shown below:

IN THE CLAIMS:

Column 26, line 36 (Claim 7), reads as follows: -- from a 6-day dose, 7-day dose, S day-dose, 14-day dose or --
Should read as follows: -- from a 6-day dose, 7-day dose, 8-day dose, 14-day dose or --

Column 27, line 6 (Claim 18), reads as follows: -- the Gestodene-containing composition comprise a hacking --
Should read as follows: -- the Gestodene-containing composition comprise a backing --

Column 27, line 11 (Claim 20), reads as follows: -- 20. The kit of claim 18, wherein the drag-containing layer --
Should read as follows: -- 20. The kit of claim 18, wherein the drug-containing layer --

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,668,925 B2
APPLICATION NO. : 11/008642
DATED : March 11, 2014
INVENTOR(S) : Langguth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1332 days.

Signed and Sealed this
Seventh Day of July, 2015

Michelle K. Lee
*Director of the United States Patent and Trademark Office*